United States Patent [19]

Gracey

[11] 4,157,088
[45] Jun. 5, 1979

[54] AUDIO RELAXER-MASSAGER

[76] Inventor: Viola N. Gracey, 2700 - 33rd St., Snyder, Tex. 79549

[21] Appl. No.: 777,106

[22] Filed: Mar. 14, 1977

[51] Int. Cl.² ............................................. A61H 1/00
[52] U.S. Cl. .................................... 128/33; 128/1 C; 128/24.1; 128/70
[58] Field of Search ................. 128/33, 68.1, 373, 395, 128/24.1, 71, 1 C

[56] References Cited

U.S. PATENT DOCUMENTS

| | | | |
|---|---|---|---|
| 1,429,443 | 9/1922 | McFaddin | 128/395 UX |
| 1,643,399 | 9/1927 | Wentworth | 128/373 X |
| 2,511,061 | 6/1950 | Hughes | 128/71 UX |
| 2,786,465 | 3/1957 | Moxley | 128/33 UX |
| 2,893,380 | 7/1959 | Walker et al. | 128/33 X |
| 2,949,108 | 8/1960 | Vecchio | 128/24.1 |
| 3,014,477 | 12/1961 | Carlin | 128/1 C |
| 3,050,051 | 8/1962 | Moxley | 128/33 |
| 3,826,250 | 7/1974 | Adams | 128/33 |

Primary Examiner—Lawrence W. Trapp
Attorney, Agent, or Firm—Berman, Aisenberg & Platt

[57] ABSTRACT

A pad designed to accommodate a human body is provided with a built-in cassette player having a recorded message giving specific instructions concerning relaxation techniques. The pad is also equipped with built-in vibrating and heating devices to massage the body of the user and assist in achieving a state of relaxation. The pad may also be equipped with an attachment for receiving an infrared lamp having a blower for directing warm air over the pad to induce relaxation and muffle surrounding noises. Appropriate controls are provided within easy reach of the user. Preferably, the pad is foldable and is provided with handles to aid in its portability.

1 Claim, 3 Drawing Figures

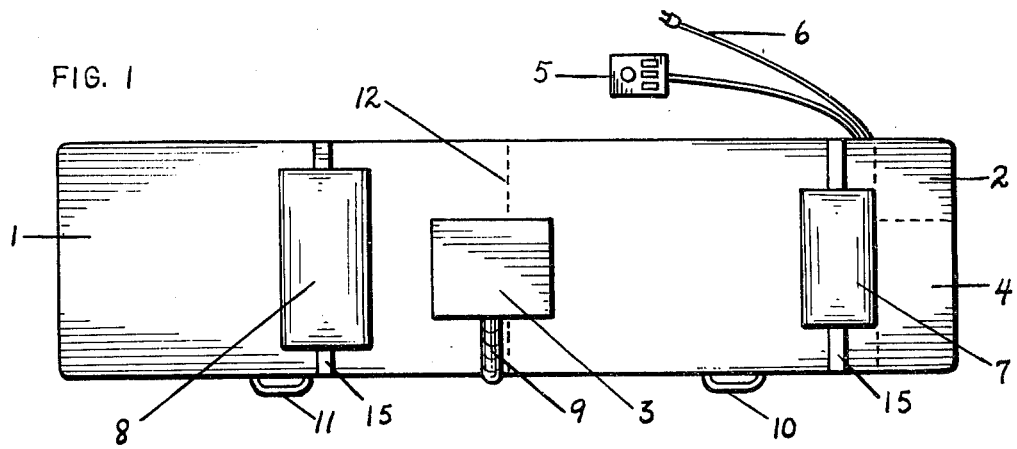
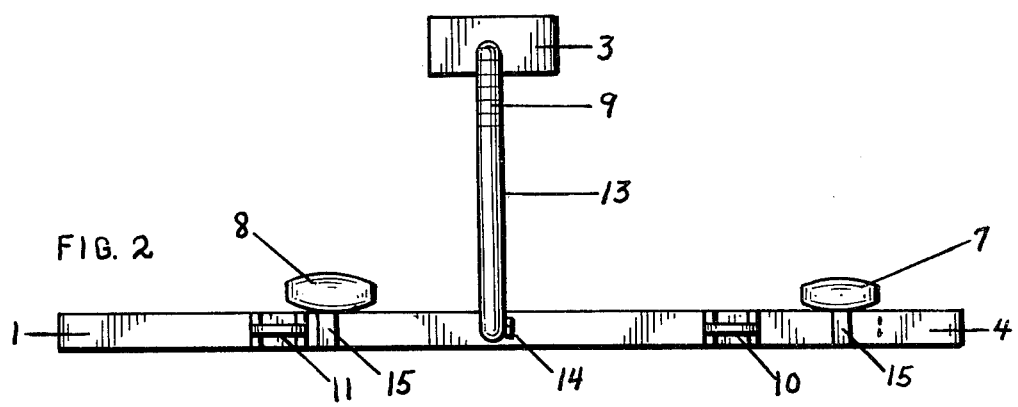
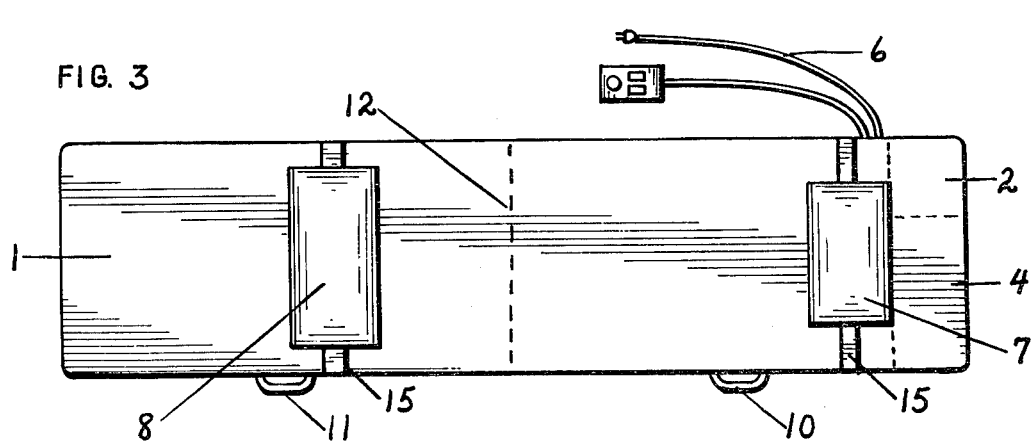

AUDIO RELAXER-MASSAGER

BACKGROUND OF THE INVENTION

While various relaxation and massaging devices have been known in the past, there has been none known which combines the massaging function with built in means for providing prerecorded relaxation instructions to the user of the device.

Accordingly, it is a principal object of the present invention to provide a body massaging device having a built-in apparatus for delivering a prerecorded set of instructions to aid in the relaxation of the user of the device.

SUMMARY OF THE INVENTION

The relaxation massaging device of the present invention comprises a pad, designed to accomodate the human body in a supine position, covered with vinyl and a rigid plastic reinforced base. A conventional massaging or vibrating device, including internally disposed heating elements, is associated with the pad so that a person lying thereon will experience the relaxing effects of the vibration massage and warmth when the appropriate controls are actuated. Built into the pad is a tape cassette player, prerecorded with specific instructions so as to advise the user thereof on how best to achieve a state of relaxation. The pad is hinged or otherwise foldable at about its lateral center line and is provided with carrying handles so as to be readily portable when in a folded condition. In one embodiment, the pad is provided with a mounting for receiving an infrared lamp having a blower for directing warm air over the pad to aid in the relaxation process and muffle surrounding noises.

BRIEF DESCRIPTION OF THE DRAWINGS

In the accompanying drawings which form part of the instant specification and which are to be read in conjunction therewith and in which like numbers refer to like parts throughout the views:

FIG. 1 is a top plan view of a first embodiment of the combination massager and relaxation device according to the present invention;

FIG. 2 is a side elevation of the device shown in FIG. 1;

FIG. 3 is a top plan view of a simplified version of the device shown in FIG. 1; and FIG. 4 is a perspective view, partially broken away of the device shown in FIG. 1.

DETAILED DESCRIPTION OF THE PREFERRED EMBODIMENTS

Referring now to FIGS. 1, 2 and 4 it will be seen that the combination massager and relaxation device of the present invention comprises a pad 1 of generally rectangular configuration, covered with a plastic material such as vinyl and having a rigid reinforced base, preferably of plastic material. The pad is provided with a standard vibration type massager, 16 with internally disposed heating elements, of types well known in the art. Built into the upper right hand corner of pad 1, as viewed in FIG. 1, is a cassette player 2 having a tape bearing prerecorded specific relaxation instructions, such as the proper positioning of the body, mind and muscle control practices, proper breathing and the like.

Mounted at about the midpoint of pad 1 by means of nut 14, is thermostatically controlled infrared heat lamp 3 having a self-contained blower for causing the flow of warm air across the surface of pad 1. Area 4 however, is completely free of heat and vibration. Lamp and blower 3 are mounted on flexible metal conduit 9, to permit adjustment of the position thereof, and rigid metal conduit 13, which in turn is attached to the side of pad 1 by means of nut 14.

At the head portion of pad 1 is disposed vinyl covered foam pillow 7 for placement under the neck of the user. A similar pillow 8 is disposed adjacent the lower end of pad 1 for positioning beneath the knees of the user. Both pillows 7 and 8 are secured in place by elastic bands 15 which extend around pad 1.

Suitable electrical controls 5 are provided within easy reach of the user of the device for controlling the degree of vibration, the heat emmanating from lamp 3, the heat emmanating from the pad itself, wich may be preferably provided with internally disposed infrared heating elements, except, as noted above, in area 4, and on-off and volume controls for the cassette player. Electrical cord 6 is provided for connection to a standard electrical outlet for providing a source of actuating electrical energy.

Disposed on the front side of pad 1 are carrying handles 10 and 11 which permit the device of the present invention to be readily transported when it is folded by means of folding element 12, preferably a hinge or the like.

Turning now to FIG. 3, there is illustrated a simplified version of the device of FIGS. 1 and 2. It will be readily seen that the device of FIG. 3 is substantially identical to that illustrated in FIGS. 1 and 2 except for the elimination of heat lamp and blower 3 along with the mounting elements therefor. In addition, electrical control 5 is simplified by the elimination of the switch controlling the heat lamp and a blower.

In a preferred form of the invention, pad 1 is 72" long, 18" wide and 2 ½" thick. Pillow 7 is 6" by 10" and 3" thick, while pillow 8 is 7" by 14" and 4" thick. Flexible metal conduit 9 is 6" long and rigid metal conduit 13 is 14" long. Elastic bands 15 are 1" wide.

In operation, the user of the device stretches out in a supine position, facing upward, with pillow 7 under his neck and pillow 8 under his knees. In this position, the right hand of the user will be in close proximity to controls 5 for actuating cassette 2 to provide the specific relaxation instructions recorded on the tape contained therein as well as the controls for heat lamp and blower 3 and the self-contained massager-vibrator and heating device within pad 1. After use, the device of the present invention may be readily stored by loosening nut 14 (in the embodiment of FIGS. 1 and 2) and removing heat lamp and blower 3 from its mounted position on the side of pad 1. Alternatively, nut 14 may be loosened just enough to permit rigid conduit 13 to be swung to a position parallel to the side of pad 1 and then retightened, so that the entire device can be stored as a unit. Pad 1 may then be folded along folding device 12 and lifted by means of handles 10 and 11 to a convenient storage area.

It has been found that the device of the present invention, having a built-in cassette player and tape providing specific relaxation practices and instructions, helps relieve body tension, aids in deep relaxation, stimulates circulation, and may temporarily relieve pains of arthritis, strains, muscular pain, and other minor aches and pains.

It will be appreciated by those skilled in the art that the subject invention may be practiced by other than the specific embodiments described above. Accordingly, it is intended that the scope of my invention be interpreted only by the claims appended hereto.

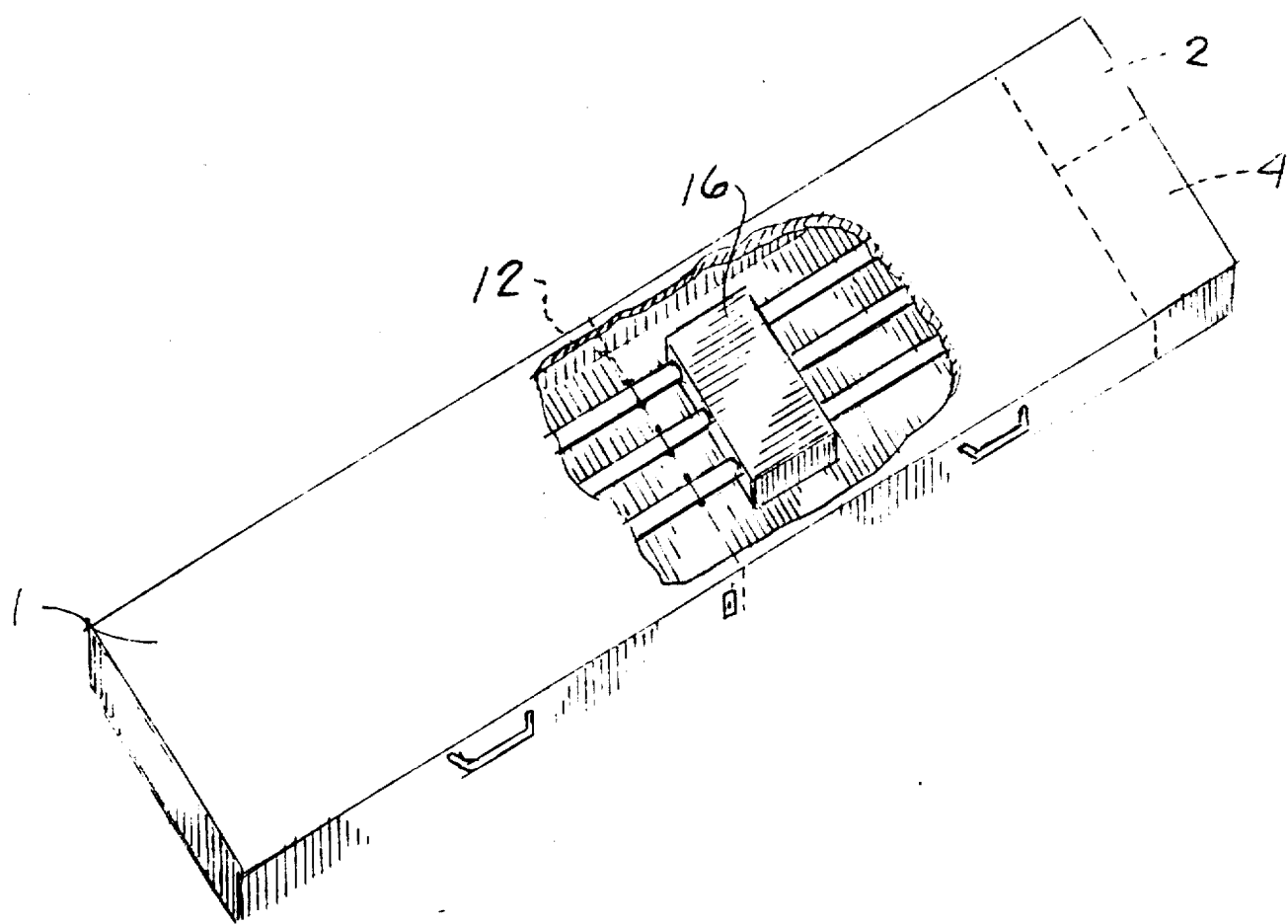

I claim:

1. A portable massaging - relaxation device, comprising:
   (a) a pad for receiving the body of the user, and having a length designed to accomodate the average human body;
   (b) means attached to said pad for inducing vibrations therein;
   (c) a compact cassette tape player disposed within said pad and adjacent the portion thereof designed to receive the head of the user, said cassette player containing a prerecorded tape with specific relaxation instructions;
   (d) first pillow means for supporting only the neck of the user;
   (e) second pillow means for supporting only the bend under the knees of the user;
   (f) detachable infrared heat lamp and blower means attached to said pad and normally extending thereabove and means for mounting said heat lamp and blower means for permitting said means to be swivelled to a position parallel to said pad for storage purposes and including a flexible neck for permitting adjustment of the position of said heat lamp and blower means;
   (g) control means disposed adjacent said pad for regulating said vibration means, said message means and said heat lamp and blower means;
   (h) means disposed within said pad to provide thermostatically controlled heat;
   (i) means permitting said pad to be folded for storage; and
   (j) handle means for transporting said pad after it has been folded.

* * * * *

UNITED STATES PATENT AND TRADEMARK OFFICE
CERTIFICATE OF CORRECTION

PATENT NO. :   4,157,088
DATED      :   June 5, 1979
INVENTOR(S):   Viola N. Gracey It is certified that error appears in the above-identified patent and that said Letters Patent are hereby corrected as shown below:

Title page, column 2, last line, "3 Drawing Figures" should read

-- 4 Drawing Figures --

In the drawings, the attached Figure 4 should be added.

Signed and Sealed this

Fifteenth Day of April 1980

[SEAL]

Attest:

SIDNEY A. DIAMOND

*Attesting Officer*       *Commissioner of Patents and Trademarks*